United States Patent [19]

Morimoto et al.

[11] Patent Number: 4,680,386
[45] Date of Patent: Jul. 14, 1987

[54] 6-O-METHYLERYTHROMYCIN A DERIVATIVE

[75] Inventors: Shigeo Morimoto; Takashi Adachi, both of Saitama; Toshifumi Asaka, Ageo; Yoshiaki Watanabe, Kodaira; Kaoru Sota, Tokorozawa, all of Japan

[73] Assignee: Taisho Pharmaceutical Co., Ltd., Tokyo, Japan

[21] Appl. No.: 789,771

[22] Filed: Oct. 21, 1985

[30] Foreign Application Priority Data

Oct. 26, 1984 [JP] Japan ................... 59-225543

[51] Int. Cl.$^4$ ............................. A61K 71/31
[52] U.S. Cl. ......................... 536/7.4; 536/7.2
[58] Field of Search ..................... 536/7.2, 7.4

[56] References Cited

U.S. PATENT DOCUMENTS 4,331,803 5/1982 Watanabe et al. ............ 536/7.2
4,349,545 9/1982 d'Ambrieres et al. ......... 536/7.4
4,496,717 1/1985 Adachi et al. ............... 536/7.2

FOREIGN PATENT DOCUMENTS 0041355 5/1981 European Pat. Off. ......... 536/7.2
0158467 3/1985 European Pat. Off. ......... 536/7.2

Primary Examiner—Johnnie R. Brown
Attorney, Agent, or Firm—Cushman, Darby & Cushman

[57] ABSTRACT

A novel 6-O-methylerythromycin A derivative represented by the formula

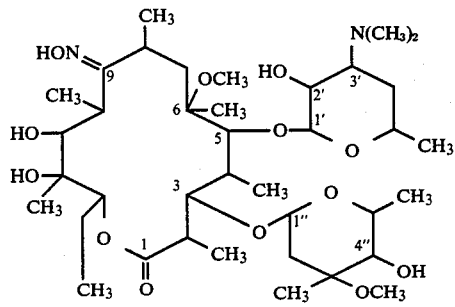

and the salts thereof are disclosed. These compounds are useful as intermediates for preparation of 6-O-methylerythromycin A and useful as antibiotics.

2 Claims, No Drawings

6-O-METHYLERYTHROMYCIN A DERIVATIVE

BACKGROUND OF THE INVENTION

The present invention relates to a 6-O-methylerythromycin A derivative which is useful as an intermediate for preparation of 6-O-methylerythromycin A and useful as an antibacterial agent.

U.S. Pat. No. 4,331,803 discloses a method for synthesis of 6-O-methylerythromycin A which is extremely useful as an antibacterial agent.

In this method, 2'-O,3'-N-bis(benzyloxycarbonyl)-N-demethylerythromycin A derived from erythromycin A is subjected, in turn, to methylation of a hydroxy group at the 6-position using methyl iodide and sodium hydride, to elimination of benzyloxycarbonyl groups at the 2'- and 3'-positions and to N-methylation under reductive conditions to give 6-O-methylerythromycin A.

However, this method lacks a high selective methylation of a hydroxy group at the 6-position and produces not a little 11-O-methyl form as major by-product. Therefore, there are drawbacks of causing low preparation yield of the objective 6-O-methylerythromycin A and causing complication in purification procedure.

As a result of the studies to decrease the formation of the by-products and to synthesize 6-O-methylerythromycin A efficiently, the present inventors have found the facts that methylation of 2'-O,3'-N-bis(benzyloxycarbonyl)-N-demethylerythromycin A, in which carbonyl group at the 9-position is modified by a substituted or unsubstituted benzyloxyimino group, takes place selectively at a hydroxy group at the 6-position to give a 6-O-methyl form in good yield, and that 6-O-methylerythromycin A 9-oxime, obtained by elimination of benzyloxycarbonyl group and substituted or unsubstituted benzyl group and by N-methylation of the 6-O-methyl form, can be easily converted to 6-O-methylerythromycin A by deoximation and this oxime form itself is a novel antibiotic having a strong antibacterial activity, and thus the present invention has been completed.

SUMMARY OF THE INVENTION

Accordingly, an object of the present invention is to provide novel 6-O-methylerythromycin A derivatives which are useful as intermediates of 6-O-methyl-erythromycin A and useful as antibiotics.

Other objects and advantages of the present invention will be apparent from the following descriptions.

DETAILED DESCRIPTION OF THE INVENTION

The present invention is illustrated in detail hereunder.

The objective compound of the present invention is an oxime compound (hereinafter referred to as Compound I) represented by the formula

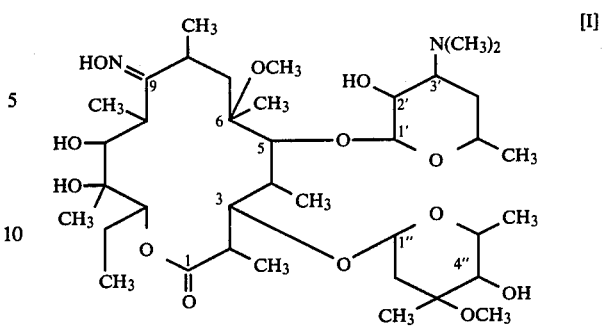

and the salts thereof.

In the present invention, the term "salt" means pharmacologically acceptable salts with organic acids such as acetic acid, propionic acids, butyric acid, trifluoroacetic acid, maleic acid, tartaric acid, citric acid, stearic acid, succinic acid, ethylsuccinic acid, methanesulfonic acid, benzenesulfonic acid, p-toluenesulfonic acid, laurylsulfonic acid, malic acid, aspartic acid, glutamic acid and the like; and inorganic acids such as hydrochloric acid, sulfonic acid, phosphoric acid, hydroiodic acid and the like.

The compound I can be synthesized, for example, by the following method: namely, a compound (hereinafter referred to as compound II) represented by the general formula

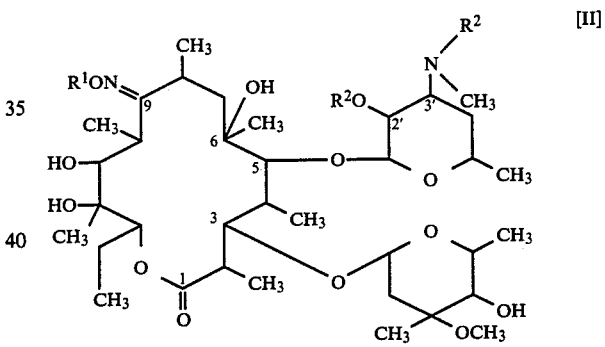

[wherein $R^1$ represents a benzyl group or a substituted benzyl group (e.g., a benzyl group substituted by 1 to 3 of halogen atoms, methoxy groups and/or nitro groups at the benzene ring), and $R^2$ represents a benzyloxycarbonyl group)] is subjected, in turn, to methylation of a hydroxy group at the 6-position, to elimination of $R^1$ and $R^2$ under reductive conditions and to reductive N-methylation in the presence of formaldehyde to give the compound I.

The above mentioned methylation of a hydroxy group at the 6-position can be carried out by the reaction of the compound II with a methylating agent in the presence of a base in a polar aprotic solvent at 0° C. to room temperature.

The polar aprotic solvent, herein, includes N,N-dimethylfomamide, dimethyl sulfoxide, hexamethylphosphoric triamide, a mixture thereof, and a mixture of one of these solvents and an inert solvent (e.g., tetrahydrofuran, 1,2-dimethoxyethane, acetonitrile, ethyl acetate and the like).

As the methylating agent, there can be used methyl iodide, dimethyl sulfate, methyl p-toluenesulfonate, methyl methanesulfonate and the like. Although excess amount of the methylating agent may be used relative to the compound II, but usually it is sufficient to use 1.2 to 2.4 molar equivalents of the methylating agent relative to the compound II.

As the base there can be used sodium hydride, potassium hydride, potassium hydroxide, sodium hydroxide and the like.

In this case, it is preferable to use 1~1.2 molar equivalents of the base reactive to the compound II in order to avoid the side-reaction.

After adding water to the reaction solution, the 6-O-methyl form which precipitated, is collected by filtration or by extraction with a hydrophobic solvent (e.g. ethyl acetate, chloroform, dichloromethane and the like). If necessary, further purification can be carried out by silica gel column chromatography or recrystallization.

The elimination of $R^1$ and $R^2$ of the 6-O-methyl form can be carried out efficiently by hydrogenation of the above mentioned 6-O-methyl form in an alcoholic solvent in the presence of palladium black or palladium carbon catalyst under a hydrogen atmosphere with stirring. This reaction can be carried out sufficiently at room temperature. The addition of formic acid, acetic acid or the like is convenient for the progression of the reaction.

Alternatively, this hydrogenation can be carried out easily in the presence of a suitable hydrogen source (e.g., ammonium formate, sodium formate, and a mixture of these formates and formic acid) and palladium carbon in an organic solvent (e.g., methanol, ethanol, N,N-dimethylformamide and the like) at room temperature with stirring.

6-O-methyl-N-demethylerythromycin A 9-oxime thus obtained can be subjected to N-methylation by the following method to give the compound I. Namely, the N-methylation can be carried out in good yield by heating 6-O-methyl-N-demethylerythromycin A 9-oxime in the presence of formic acid and formaldehyde in an inert solvent (e.g., chloroform, methanol, ethanol and the like) with stirring.

Alternatively, after the elimination of $R^1$ and $R^2$ of the 6-O-methyl form, the hydrogenation is continued by the addition of an excess amount of formaldehyde to carry out N-methylation efficiently.

After completion of the reaction, the reaction solution is poured into water, and the pH of the solution is adjusted to 10 to 10.3 to precipitate the compound I. Alternatively, the reaction solution is extracted with the same hydrophobic solvent as that used above to give the compound I.

Two isomers for the 9-oxime group exist in the compound of formula I. The compound I of the present invention is not limited to only one of both isomers and includes either of both isomers and a mixture thereof. If necessary, the mixture of both isomers is crystallized from ethanol or ethanol-petroleum ether to isolate the major isomer efficiently.

The pharmacologically acceptable acid salts of the compounds of this invention are readily prepared by treating the compound I with at least an equimolar amount of the corresponding acid described above in a reaction-inert solvent or, in the case of the hydrochloride salts, with pyridinium hydrochloride. The acid salts recovered by filtration if they are insoluble in the reaction-inert solvent, by precipitation without solvent for the acid salt, or by evaporation of the solvent.

The compound I can be converted to 6-O-methylerythromycin A easily by deoximation using sodium hydrogen sulfite, titanium trichloride-ammonium acetate, nitrous acid and the like.

The compound II of the starting material can be prepared, for example, by the following method: Namely, 2'-O,3'-N-bis(benzyloxycarbonyl)-N-demethylerythromycin A, derived from erythromycin A according to the method of E. H. Flynn [J. Am. Chem. Soc., 77, 3104 (1955)], is subjected to oximation using hydroxylamine hydrochloride and a suitable base followed by etherification with a benzyl halide of formula $R^1X$ (wherein $R^1$ is as defined above and X is a halogen atom) to give the compound II. Example of the base includes imidazole, anhydrous sodium acetate, anhydrous potassium acetate and the like. The oximation is carried out in methanol at room temperature to the boiling point of methanol or below. This reaction proceeds at room temperature sufficiently, but heating to about 40° to 50° C. promotes the proceeding of the reaction.

Since the progression of the reaction can be followed by a silica gel thin layer chromatography, the reaction is turned off after disappearance of the 9-ketone form.

After the reaction, the methanol is evaporated, and the residue is extracted with the same hydrophobic solvent as that used above to give the 9-oxime form.

The 9-oxime form thus obtained exists in the anti- and syn-forms for an oxime group at the 9-position, and it is easy to separate the major isomer, which is more stable, by crystallization. Although the other isomer can be isolated by silica gel column chromatography, this isomer is very unstable and has the property of being changeable to the major isomer. For the purpose of the present invention, the oxime form may exist in either of two isomers and in a mixture thereof.

In the case where the compound II of the O-substituted oxime form is obtained by etherification of the oxime form, there may be used a wide variety of organic solvents, preferably acetone, tetrahydrofuran, N,N-dimethylformamide, dimethyl sulfoxide and the like.

Examples of the benzyl halide ($R^1X$) are benzyl chloride, benzyl bromide, p-methoxybenzyl chloride, o-chlorobenzyl chloride, m-chlorobenzyl chloride, p-chlorobenzyl chloride, 2,4-dichlorobenzyl chloride, p-bromobenzyl chloride, m-nitrobenzyl chloride, p-nitrobenzyl chloride and the like. The amount of the benzyl halide used is 1 to 1.2 molar equivalents amount. Examples of the base are sodium hydride, potassium hydride, sodium hydroxide, potassium hydroxide and the like. The amount of the base is 1 to 1.2 molar equivalents amount. The etherification is carried out at −15° C. to room temperature.

After completion of the etherification, the reaction solution is poured into water to give the precipitate, which is then collected by filtration or extracted with the same hydrophobic solvent a that used above to give the compound II. If necessary, further purification is carried out by crystallization or silica gel column chromatography.

Alternatively, erythromycin A is reacted with hydroxylamine hydrochloride in the presence of a suitable base (e.g., imidazole, anhydrous sodium acetate, anhydrous potassium acetate, etc.) to give erythromycin A 9-oxime. This is etherified according to the same manner described above to give the O-substituted oxime form, which is then reacted with an excess amount of benzyl chloroformate of formula R²Cl (wherein R² is as defined above) in a conventional manner to give the compound II.

As stated above, the compound I of the present invention can be easily synthesized in good efficiency, purified without any complicated procedure, and converted into 6-O-methylerythromycin A easily by deoximation so that this compound I is useful as an intermediate for preparation of antibacterial agent.

Furthermore, the compound I and the salts thereof themselves have a strong antibacterial activity. Particularly, these compounds are far superior to erythromycin A or erythromycin A 9-oxime in terms of antibacterial activity by oral administration. Therefore, the compound I and the salts thereof are useful as a therapeutic agent for infectious diseases caused by gram-positive bacteria, mycoplasma or pathogenic bacteria sensitive to the compound I in man and animals.

For these purposes the compound I and the salt thereof may be administered orally or parenterally, e.g. by subcutaneous or intramuscular injection, in a conventional dosage form such as tablet, capsule, powder, troche, dry mixes, ointment, suspension or solution prepared according to conventional pharmaceutical practices.

The compound I can be administered orally or parenterally at a dosage of from about 1 mg/kg to about 200 mg/kg of body weight per day and the preferred range from about 5 mg/kg to about 50 mg/kg of body weight per day.

The following experiments show the fact that the compound I has in vitro and in vivo antibacterial activity.

Experiment 1

(In vitro antibacterial activity)

The antibacterial activity of the compound I against various bacteria was measured using sensitive media (produced by Eiken Co.) according to the MIC method specified by the Japan Chemotherapeutic Society. Erythromycin A was used as a control.

The results, indicated as MIC value (minimum inhibitory concentration, mcg/ml), are shown in Table 1.

TABLE 1

| | In vitro antibacterial activity MIC (mcg/ml) | |
|---|---|---|
| Bacteria tested | Erythromycin A | Compound I |
| Bacillus cereus ATCC 9634 | 0.2 | 0.1 |
| Bacillus subtilis ATCC 6633 | 0.1 | 0.1 |
| Staphylococcus aureus FDA 209P | 0.2 | 0.1 |
| Staphylococcus aureus Smith No. 4 | 0.1 | 0.1 |
| Streptococcus epidermidis sp-al-1 | 0.2 | 0.2 |
| Streptococcus faecalis 8043 | ≦0.05 | ≦0.05 |
| Escherichia coli NIHJ JC-2 | 50 | 50 |

Experiment 2

(In vivo antibacterial activity)

10 male ICR mice (Charles River) being of the average body weight 23 g were used for each group. *Staphylococcus aureus* Smith No. 4 was grown on heart infusion agar medium at 37° C. for 18 hours. The bacteria were suspended in BSG (containing 8.5 g of NaCl, 300 mg of $KH_2PO_4$, 600 mg of $Na_2HPO_4$, 100 mg of gelatin and 1000 ml of water) to show $6 \times 10^7$ cfu/ml (containing 5% of mucin). The bacterial suspension (0.5 ml) was injected intraperitoneally to each groups of mice for infection. Erythromycin A and erythromycin A 9-oxime were used as control. An hour after infection, each compound was administered orally to different groups of animals in the specified amounts to study its therapeutic effect.

The results are shown in Table 2.

The therapeutic effect of the drugs was judged by the $LD_{50}$ value calculated from the number of mice surviving for 7 days after the infection according to the method of Litchfield-Wilcoxon.

TABLE 2

| | In vivo antibacterial activity | | |
|---|---|---|---|
| | Drug | | |
| Dose (mg/mouse) | Erythromycin A | Erythromycin A 9-oxime | Compound I |
| 4 | 10/10 | — | — |
| 2 | 8/10 | 7/10 | — |
| 1 | 1/10 | 3/10 | — |
| 0.8 | — | — | 7/10 |
| 0.5 | — | 0/10 | — |
| 0.4 | — | — | 4/10 |
| 0.2 | — | — | 1/10 |
| ED50 (mg/mouse) | 1.517 | 1.418 | 0.516 |
| Confidence limits (p = 95%) | 1.146–2.008 | 0.975–2.064 | 0.319–0.833 |

Subsequently, the present invention will be more concretely illustrated by the following Referencial Examples and Examples.

REFERENCIAL EXAMPLE 1

(1) A mixture of 49.4 g of 2'-O,3'-N-bis(benzyloxycarbonyl)-N-demethylerythromycin A, 17.38 g of hydroxylamine hydrochloride, 18.73 g of imidazole and 250 ml of methanol was stirred at room temperature for 3 days, and then refluxed under heating for 30 minutes. After completion of the reaction, most of the methanol was evaporated, and then 250 ml of ethyl acetate and 250 ml of a 5% aqueous sodium bicarbonate solution were added. The ethyl acetate layer was separated, washed, in turn, with 250 ml of a saturated aqueous sodium bicarbonate solution and 250 ml of a saturated aqueous sodium chloride solution, and dried over anhydrous magnesium sulfate. The ethyl acetate was evaporated under reduced pressure, there was obtained a residue which was then crystallized from dichloromethane to give 34.67 g of 2'-O,3'-N-bis(benzyloxycarbonyl)-N-demethylerythromycin A 9-oxime.

m.p. 152°~154° C.

Since this compound shows a single spot by thin layer chromatorgraphy (TLC) analysis (chromatography plate produced by Merck Co.,: silica gel $_{60}F_{254}$; developing solvent: chloroform-methanol=20:1), it is an isomer for the 9-oxime.

(2) The mother liquor from which the crystals was removed in the above item (1), was concentrated to dryness under reduced pressure, and the residue was applied to a silica gel column chromatography [eluent: :ethyl acetate-n-hexane (2:1)]. TLC analysis (as described above) was conducted, and the eluting fractions showing the Rf value 0.21 were collected, and concentrated to dryness to give 3.0 g of the compound which was identical with that obtained in the above item (1).

On the other hand, the fractions showing the Rf value 0.12 were combined, and concentrated to dryness to give 0.54 g of the other isomer of the compound obtained in the above item (1) as a white foam.

REFERENTIAL EXAMPLE 2

250 g of 2'-O,3'-N-bis(benzyloxycarbonyl)-N-demethylerythromycin A, 124.6 g of anhydrous sodium acetate and 87.93 g of hydroxylamine hydrochloride in 1000 ml of methanol were stirred at room temperature for 6 days. The methanol was evaporated under reduced pressure to reduce to one-half the volume of the reaction solution, and 3000 ml of water was poured thereto. The precipitate which formed was collected by filtration, and washed, in turn, with 500 ml of water, 1500 ml of a saturated aqueous sodium bicarbonate solution and 500 ml of water. This was dried and crystallized from dichloromethane-n-hexane to give 190 g of 2'-O,3'-N-bis(benzyloxycarbonyl)-N-demethylerythromycin A 9-oxime.

REFERENTIAL EXAMPLE 3

A solution of 255 g of erythromycin A, 120.7 g of hydroxylamine hydrochloride and 130.1 g of imidazole in 850 ml of methanol was refluxed with stirring for 4 hours. The methanol was evaporated under reduced pressure. To the residue were added 2000 ml of ethyl acetate and 1500 ml of water, and the pH of the solution was adjusted to about 9 with 2N sodium hydroxide. Subsequently, the ethyl acetate layer was separated, washed with 2000 ml of a saturated aqueous sodium chloride solution and dried over anhydrous magnesium sulfate.

The ethyl acetate was evaporated under reduced pressure, the residue thus obtained was crystallized from dichloromethane-n hexane to give 197.7 g of erythromycin A 9-oxime.

m.p. 153°~155° C.

REFERENTIAL EXAMPLE 4

3 g of 6-O-methylerythromycin A 9-oxime and 3.27 g of sodium hydrogen sulfite were dissolved in a mixture of 30 ml of ethanol and 30 ml of water, and then the mixture was refluxed with stirring for 6 hours.

The mixture was cooled to room temperature, 60 ml of water was added, and the pH of the mixture was adjusted to 10 or above with a saturated aqueous sodium carbonate solution. The precipitate which formed was collected by filtration, washed throughly with water, and recrystallized from ethanol to give 2.01 g of 6-O-methylerythromycin A as crystals.

m.p. 223°~225° C.

EXAMPLE 1

(1) To a solution of 170 g of 2'-O,3'-N-bis(benzyloxycarbonyl)-N-demethylerythromycin A 9-oxime and 30 g of o-chlorobenzyl chloride in 680 ml of N,N-dimethylformamide was added 12.3 g of a 85% potassium hydroxide powder under ice water cooling with stirring. The stirring was continued for further 3 hours, and then the reaction solution was poured into 3500 ml of water with stirring.

The precipitate which formed was collected by filtration, the filtrate was washed, in turn, with 500 ml of water, 2000 ml of a 15% aqueous ethanol and 500 ml of water, and then dried to give 189.7 g of crude crystals of 2'-O,3'-bis(benzyloxycarbonyl)-N-demethylerythromycin A 9-[O-(o-chlorobenzyl)oxime].

m.p. 111°~113° C. (recrystallized from ethyl acetate-n hexane) (2) 140 g of the compound obtained in the above item (1) and 10.05 ml of methyl iodide were dissolved in 560 ml of a mixture of dimethyl sulfoxide and tetrahydrofuran (1:1), and 9.83 g of a 85% potassium hydroxide powder was added under ice-water cooling with stirring, and the stirring was continued for additional 2 hours. Thereafter, 28 ml of triethylamine was added at 0°~5° C., the mixture was stirred at room temperature for an hour, and then the reaction solution was poured W into a mixture of 1800 ml of ethyl acetate and 900 ml of a saturated aqueous sodium chloride solution. The ethyl acetate layer was separated and subsequently washed, in turn, with 900 ml of a saturated aqueous sodium chloride solution, 900 ml (×2) of an aqueous 1N hydrochloric acid solution (saturated with sodium chloride), 900 ml of a saturated aqueous sodium chloride solution, 900 ml of a saturated aqueous sodium bicarbonate solution and 900 ml of a saturated aqueous sodium chloride solution. The ethyl acetate layer was dried over anhydrous magnesium sulfate, concentrated to dryness and recrystallized from isopropyl alcohol to give 122 g of 6-O-methyl-2'-O,3'-N-bis(benzyloxycarbonyl)-N-demethylerythromycin A 9-[O-(o-chlorobenzyl)oxime].

m.p. 191°~193° C.

(3) 80 g of the compound obtained in the above item (2) was dissolved in a mixture of 560 ml of methanol, 20 ml of water and 20 ml of acetic acid, and 8 g of palladium black was added. The mixture was stirred under a hydrogen atmosphere at room temperature for 7 hours. After completion of the reaction, the catalyst was separated by filtration and washed with 200 ml of methanol. The filtrate and washings were combined, 1000 ml of water was added, and the pH of the solution was adjusted to 10 to 10.3 with an aqueous 1N sodium hydroxide solution. The precipitate which formed was collected by filtration, washed with water, dried and recrystallized from ethanol to give 47.1 g of 6-O-methyl-N-demethylerythromycin A 9-oxime.

m.p. 247°~249° C.

Mass(SIMS) m/e=749 (MH+) $^1$H-NMR (200 MHz, CDCl$_3$) $\delta$=2.41 (3H, s, NCH$_3$), 3.10 (3H, s, 6—OCH$_3$), 3.32 (3H, s, 3″—OCH$_3$) $^{13}$C-NMR (50.3 MHz, C$_5$D$_5$N) $\delta$=169.2 (C-9), 79.5 (C-6), 51.6 (C$_6$—OCH$_3$), 49.7 (C$_{3''}$—OCH$_3$) 33.8 (NCH$_3$), 25.8 (C-8), 20.7 (C$_6$—CH$_3$)

Elementary Analysis for C$_{37}$H$_{68}$N$_2$O$_{13}$ Calcd. (%): C 59.34, H 9.15, N 3.74;Found (%): C 59.35, H 8.87, N 3.78.

(4) A mixture of 7.49 g of the compound obtained in the above item (3), 0.755 ml of formic acid, 5.14 ml of a 35% aqueous formaldehyde solution and 100 ml of methanol was refluxed with stirring for 5 hours in order to proceed the reaction.

After completion of the reaction, the reaction solution was cooled to room temperature, and the methanol was evaporated under reduced pressure. After addition of 100 ml of ice water, the pH of the solution was adjusted to about 10 with an aqueous 1N sodium hydroxide solution.

Subsequently, the solution was extracted with dichloromethane, and the extract was washed with water, dried, concentrated and crystallized from ethanol-petroleum ether to give 7.13 g of 6-O-methylerythromycin A9-oxime.

m.p. 248°~251° C. (melted at 169°~171° C., resolidified at 180°~185° C., and melted again at 248°~251° C.) IR $v_{max}^{KBr}$ cm$^{-1}$: 3400, 1730, 1625, $^1$H-NMR (400 MHz, CDCl$_3$) δ=2.29 (6H, s, N(CH$_3$)$_2$), 3.11 (3H, s, 6OCH$_3$), 3.33 (3H, s, 3″—OCH$_3$)

$^{13}$C-NMR (50.3 MHz, CDCl$_3$) δ=170.1 (C-9), 78.8 (C-6), 51.2 (C$_6$—OCH$_3$), 49.5 (3″—OCH$_3$), 40.4 (N(CH$_3$)$_2$), 25.4 (C-8), 20.0 (C$_6$—CH$_3$) Mass (SIMS) m/e=763 (MH$^+$)

Elementary analysis for C$_{38}$H$_{70}$N$_2$O$_{13}$ Calcd. (%): C 59.82, H 9.25, N 3.67; Found (%): C 59.83, H 8.85, N. 3.58.

EXAMPLE 2

(1) 20 g of 2′-O,3′-N-bis(benzyloxycarbonyl)-N-demethylerythromycin A 9-oxime and 3.85 g of o-chlorobenzyl chloride were dissolved in 60 ml of a mixture of dimethyl sulfoxide and 1,2-dimethoxyethane (1:1), and 1.55 g of a 85% potassium hydroxide powder was added under ice-water cooling with stirring.

The mixture was stirred for further 2 hours, and then 3 ml of methyl iodide was added, followed by the addition of 1.58 g of a 85% potassium hydroxide powder. After stirring was continued for further 3 hours, the reaction solution was poured into a mixture of 300 ml of ethyl acetate and 150 ml of a saturated aqueous sodium chloride solution. The ethyl acetate layer was separated, washed with 150 ml of a saturated aqueous sodium chloride solution and dried over anhydrous magnesium sulfate.

The ethyl acetate layer was evaporated under reduced pressure, and then the residue was recrystallized from isopropyl alcohol to give 17.1 g of 6-O-methyl-2′-O,3′-N-bis(benzyloxycarbonyl)-N-demethylerythromycin A 9-[O-(o-chlorobenzyl)oxime].

(2) 11.4 g of the compound obtained in the above item (1) and 6.04 g of 10% palladium carbon (containing 52.9% of water) were suspended in 46 ml of N,N-dimethylformamide, and then a mixture of 1.26 g of ammonium formate and 6 ml of formic acid was added dropwise at 40°~45° C. with stirring over an hour. After stirring was continued at room temperature for further 3 hours, the catalyst was separated by filtration. To the filtrate was added 150 ml of water, the pH of the solution was adjusted to about 11 with 5N sodium hydroxide solution. The precipitate which formed was collected by filtration, washed throughly with water, dried and crystallized from ethanol to give 6.1 g of 6-O-methyl-N-demethylerythromycin A 9-oxime.

(3) By N-methylation of the compound obtained in the above item (2) according to the procedure similar to that of Example 1(4), there was obtained 5.5 g of 6-O-methylerythromycin A 9-oxime.

EXAMPLE 3

(1) To a solution of 60 g of erythromycin A 9-oxime in 150 ml of N,N-dimethylformamide was added 14.19 g of o-chlorobenzyl chloride under ice-cooling with stirring, followed by 5.82 g of a 85% potassium hydroxide powder. The stirring was continued for further 3 hours, and then the reaction solution was poured into a mixture of 1500 ml of ethyl acetate and 2000 ml of a saturated aqueous sodium chloride solution.

The ethyl acetate layer was separated, washed twice with 500 ml of a saturated aqueous sodium chloride solution, dried over anhydrous magnesium sulfate and concentrated to dryness to give 66.98 g of erythromycin A 9-[O-(o-chlorobenzyl)oxime] as a white powder.

m.p. 114°~117° C. (recrystallized from n-hexane)

(2) 5 g of the compound obtained in the above item (1) was dissolved in 8.5 ml of dioxane, and 5.77 g of sodium bicarbonate was added. To the mixture was added dropwise 8.14 ml of benzyl chloroformate at 55°~65° C. with stirring. After completion of the addition, the mixture was stirred at 65° C. for an hour and then cooled to room temperature.

To the mixture was added 10 ml of dichloromethane, the solid which formed was separated by filtration, and 80 ml of n-hexane was added to the filtrate. The crystals which formed was collected by filtration to give 5.92 g of 2′-O,3′-N-bis(benzyloxycarbonyl)-N-demethylerythromycin A 9-[O-(o-chlorobenzyl)oxime].

This compound was identical with the compound obtained in Example 1(1).

(3) The compound obtained in the above item (2) was subjected to O-methylation, reduction and N-methylation according to Example 1(2), (3) and (4) to give 2.05 g of 6-O-methylerythromycin A 9-oxime.

EXAMPLE 4

(1) To a solution of 20.06 g of 2′-O,3′-N-bis(benzyloxycarbonyl)-N-demethylerythromycin A 9-oxime and 3.37 g of benzyl chloride in 150 ml of dry N,N-dimethylformamide was added dropwise 1.25 g of a suspension of 50% sodium hydride in oil (liquid paraffin) at room temperature with stirring.

After stirring for further an hour, the reaction solution was poured into 600 ml of a saturated aqueous sodium bicarbonate solution, and extracted, in turn, with 300 ml of ethyl acetate, 200 ml of the one and 100 ml of the one. The ethyl acetate layers were combined, washed 3 times with 300 ml of a saturated aqueous sodium chloride solution, and dried over anhydrous magnesium sulfate. The ethyl acetate was evaporated under reduced pressure, and the residue thus obtained was purified by a silica gel column chromatography (silica gel 60 produced by Merck Co., 70~230 mesh; eluent: ethyl acetate - n-hexane=1:2~1: 1 to give 17.92 g of 2′-O,3′-N-bis(benzyloxycarbonyl)-N-demethylerythromycin A 9-[O-benzyloxime] as a white foam.

m.p. 105°~107° C. (recrystallized from ethyl acetate-petroleum ether)

(2) 5.47 g of the compound obtained in the above item (1) and 13.7 g (6 ml) of methyl iodide were dissolved in 120 ml of a mixture of dimethyl sulfoxide and tetrahydrofuran (1:1), and then 340 mg of a suspension of 60% sodium hydride in oil (liquid paraffin) was added at room temperature with stirring. After stirring was continued for further an hour, the reaction solution was poured into 200 ml of a saturated sodium bicarbonate aqueous solution, and extracted twice with 200 ml of ethyl acetate. The ethyl acetate layers were combined, washed 3 times with 200 ml of a saturated aqueous sodium chloride solution, and dried over anhydrous magnesium sulfate. The ethyl acetate was evaporated under reduced pressure, and the residue thus obtained was purified by a silica gel column chromatography (silica gel 60 produced by Merck Co., 70~230 mesh; eluent: ethyl acetate - n-hexane=1:3) to give 3.83 g of 6-O-methyl-2′O3′-N-bis(benzyloxycarbonyl)-N-demethylerythromycin A 9-O-benzyloxime as a white foam.

m.p. 154.5°~156° C. (recrystallized from diethyl ether - petroleum ether)

(3) 2.04 g of the compound obtained in the above item (2) was dissolved in 20 ml of ethanol. To this were added 5 ml of water containing 0.21 ml of acetic acid and 0.723 g of sodium acetate and 0.408 g of palladium black.

Subsequently, the mixture was stirred vigorously at 60° C. under a hydrogen atmosphere for 2 hours, 5 ml of 35% aqueous formaldehyde solution was added, and the mixture was stirred at 60° C. under a hydrogen atmosphere for further 2 hours. After completion of the reaction, the catalyst was separated by filtration. To the filtrate was added 150 ml of a 5% aqueous sodium bicarbonate solution, and then the mixture was extracted, in turn, with 150 ml of ethyl acetate, 50 ml of the one and 50 ml of the one.

The ethyl acetate layers were combined, washed 3 times with 100 ml of a saturated aqueous sodium chloride solution, dried over anhydrous magnesium sulfate and concentrated to dryness. The residue thus obtained was crystallized from ethanol - petroleum ether to give 0.989 g of 6-O-methylerythromycin A 9-oxime.

What is claimed is:

1. A 6-O-methylerythromycin A derivative represented by the formula

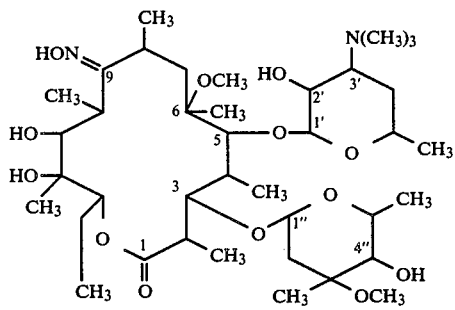

and the salts thereof.

2. A 6-O-methylerythromycin A according to claim 1, wherein the salts are pharmacologically acceptable salts with organic acids or inorganic acids.

* * * * *

UNITED STATES PATENT AND TRADEMARK OFFICE
CERTIFICATE OF CORRECTION

PATENT NO. : 4,680,386
DATED : July 14, 1987
INVENTOR(S) : Morimoto et al.

It is certified that error appears in the above-identified patent and that said Letters Patent is hereby corrected as shown below:

Column 6,
Line 36, "Referencial" should read -- Referential --;
Line 38, "REFERENCIAL" should read -- REFERENTIAL --

Column 12,
Lines 5-15, that portion of the formula reading " 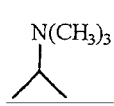 " should read -- 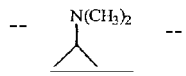 --

Signed and Sealed this

Sixth Day of April, 2004

JON W. DUDAS
*Acting Director of the United States Patent and Trademark Office*